United States Patent [19]

Korkis

[11] 3,984,538
[45] Oct. 5, 1976

[54] HAIR CONDITIONING SHAMPOO CONTAINING CHAMOMILE EXTRACT AND UREA OR THIOUREA

[75] Inventor: George Noel Korkis, Paramus, N.J.

[73] Assignee: American Cyanamid Company, Stamford, Conn.

[22] Filed: Dec. 23, 1974

[21] Appl. No.: 535,937

[52] U.S. Cl. .................................. 424/74; 424/70
[51] Int. Cl.² ........................................ H61K 7/06
[58] Field of Search ............................. 424/70, 74

[56] References Cited
UNITED STATES PATENTS

| | | | |
|---|---|---|---|
| 3,243,346 | 3/1966 | Beckmann et al. | 424/70 |
| 3,590,122 | 6/1971 | Roberts et al. | 424/70 |
| 3,650,280 | 3/1972 | Roberts et al. | 424/70 X |

*Primary Examiner*—V. D. Turner
*Assistant Examiner*—Vera C. Clarke
*Attorney, Agent, or Firm*—John Engelmann

[57] ABSTRACT

Improved hair shampoo composition containing extract of chamomile in combination with urea, having hair conditioning effects and special curl retention properties.

5 Claims, No Drawings

HAIR CONDITIONING SHAMPOO CONTAINING CHAMOMILE EXTRACT AND UREA OR THIOUREA

BACKGROUND OF THE INVENTION

This invention relates to an improved hair shampoo composition and more particularly to an improved hair shampoo composition with hair conditioning effects and special curl retention properties. More particularly it relates to an improved shampoo composition comprising extract of chamomile (Matricaria) in combination with urea.

Shampoos generally are aqueous compositions with cleansing agents and with other components or additives present for the purpose of improving performance with respect to the cleansing action on the hair and scalp and insofar as possible, to leave the hair in the desired, pleasing and satisfactory condition.

To be commercially acceptable, of course, it must be pleasant to use, producing a good foam or lather, must be easily rinsed from the hair with water, and it should leave the hair lustrous with a pleasant feel and in an easily combable and manageable condition.

To improve the results in using hair shampoo compositions, various agents are often added to improve the condition of the hair in various respects. In some instances creme rinse formulations or final sprays have been developed to achieve the desired conditioning effect, including improvement in manageability and wave set retention. Although various agents have been incorporated in shampoo compositions to give improved effects generally completely satisfactory results have been difficult to achieve.

Thus, it is an object of the invention to provide a liquid shampoo composition which is pleasant to use and which leaves the hair in a soft, lustrous, easily manageable condition with a pleasant feel and which, in addition, improves the retention of curls, for example, after curling under the hair drier.

The invention is based on aqueous shampoo compositions with amphoteric and nonionic surfactants as cleansing agents and containing in addition chamomile extract in combination with urea or thiourea.

The improved shampoo compositions of the invention thus provide shampoos which have good lathering effects, and easy to use, have good rinseability and leave the hair in a lustrous condition with a soft and silky feel, easily manageable and with improved curl retention or wave set effects. The shampoo compositions of the invention may be prepared to be effective either in acidic pH range (pH 4.5 to 6.5) or the alkaline pH range (pH 7.0 to 8.5). This is a desirable effect in that depending on the color of the hair, a special improvement results in highlighting the color of the hair, for example, in the acidic range, blonde hair acquires special brilliance with a warm blonde appearance, while in the alkaline pH range, brown hair appears a warmer brown in both instances with a desirable highlighting effect.

A special feature of the shampoo composition is an improvement in curl retention time or wave set retention.

The shampoo compositions of the invention, in addition to the novel combination of the extract of chamomile and urea or thiourea, are made up with known commercially available conventional aqueous shampoo components, for example, with amphoteric or nonionic surfactants as the primary cleansing agent fraction.

In addition, of course conventional conditioning agents, dispersants, emulsifiers, opacifiers, thickeners, preservatives, components for pH control, colorants, fragrance material, etc, may also be used.

Amphoteric detergents have been previously used in shampoo formulations where desirable and satisfactory cleansing action results. In addition to the detergent effect, it is also understood that they also impart at least to some degree conditioning properties to the mixture. As amphoteric surfactants, there may be used a variety of amphoteric compounds, for example, compounds of the betaine type as disclosed in U.S. Pat. No. 3,225,074. An example of such a betaine suitable as an amphoteric surfactant in shampoo compositions is the betaine derived from coconut fatty acids which may be identified as N-(lauramidopropyl)-N,N-dimethyl-N-carboxymethylammonium betaine; such an amphoteric surfactant is available commercially, identified as Tegobetaine C Amphoteric Surfactant, from the Goldschmidt Chemical Company. As further examples of amphoteric compounds which may be used as amphoteric surfactants in shampoo formulations are those of the imidazoline type as disclosed in U.S. Pat. No. 2,781,354. A variety of such agents are available commercially under the commercial designation "Miranol" Amphoteric Surface Active Agents.

Using these amphoteric surfactants, pH adjustments of the shampoo formulation may be easily made by the addition of various appropriate organic acids and bases such as alkanolamines.

As detergents of the nonionic type, those referred to generally as the alkanolamide type have a wide application. These are generally identified as condensation products of alkanolamines with long chain fatty acids, typical products being mixtures resulting from the reaction of diethanolamine and a long chain fatty acid. The condensation of diethanolamine with a long chain fatty acid such as lauric acid gives a typical compound identified as lauryl diethanolamide. Depending on the purity and the method of preparation, certain amine fatty acid condensation products containing as high as 85 to 90 percent of the alkanolamide are referred to as "high purity" or "super amides." Such products are often used in shampoos; in addition to detergent action they are considered also to have some hair conditioning effects.

Long chain fatty amine oxides further identified as higher alkyl dialkylamine oxides also find application in shampoo compositions and are believed to enhance conditioning effect to some extent.

Although various amphoteric and nonionic surfactants are suitable in the shampoo compositions of the invention, the shampoo compositions used as illustrative of the invention will be based primarily on the use of an amphoteric material as identified above as the major cleansing agent component with only minor amounts of the nonionic surfactant. The combination of extract of chamomile with urea or thiourea for use in a shampoo formulation to give the superior effects of the shampoo compositions of the invention is novel and gives essentially unique effects, particularly with reference to curl retention properties. This of course, is in addition to the generally satisfactory results in the use of the shampoo formulations with respect to leaving the hair in a soft, pleasant, easily manageable condition and with imparting lustrous shine and color highlights.

In the shampoo compositions from about 1 to 5 parts of the fluid extract of chamomile is used. This may be in the form of the natural chamomile extract obtainable for example, as a 25 percent solution. The chamomile may be in the form of a natural or synthetic oil of chamomile.

In the compositions from about 1 part to 3 parts per 100 parts of the composition of urea or thiourea may be used. A practical and preferable ratio of 25 percent chamomile extract to thiourea is in the range of 3 to 2.

As stated above, various other conventional additives as are used in the shampoo art may also be present.

The improved shampoo compositions of the invention are described as aqueous shampoo compositions. The unique feature is the combination of the extract of chamomile with urea or thiourea; although described primarily as a component of an aqueous shampoo compositions can be made up as a lotion, a creme, a pack, a concentrate, or even in the form of a rinse, and will be applicable then as a hair conditioning component suitable for application in an aqueous shampoo composition or otherwise as a hair conditioning agent.

The invention is further illustrated by the Examples which follow.

In the Examples, it is understood that extract of chamomile refers to the extract of German or Hungarian chamomile, otherwise identified as Matricaria; extract of chamomile designated as, common-, English-, or Roman, is a different product. In all the examples the extract of Matricaria is used.

EXAMPLE 1

Preparation of Shampoo Composition (With Chamomile Extract and Urea)

The following components were combined to form an aqueous shampoo composition at a basic pH.

|  | Parts |
|---|---|
| Amphoteric Detergent (1) | 50.0 |
| Nonionic amine oxide detergent (2) | 4.0 |
| Chamomile Extract (3) | 3.0 |
| Urea | 2.0 |
| Triethanolamine (85%) | 1.0 |
| Nonionic emulsifier (4) | 1.5 |
| Perfume | 0.3 |
| Water to make | 100 parts total |

(1) Tegobetaine C Amphoteric Detergent.
(2) Aromox c/12W bis(2-hydroxyethyl)cocoamine oxide
(3) Chamomile extract, German —25 percent
(4) Tween 20, emulsifier, polyoxyethylene sorbitan monolaurate.

This resulted in a shampoo composition with a pH about 8.3.

The mixture remained clear with no apparent change in appearance or performance after storage about 40 days at 3°C., RT and 40°C.

The above formulation may also be prepared with a modification wherein 2 parts of polyethylene glycol (6000) distearate are also included, resulting in some increase in conditioning effect.

EXAMPLE 2

Preparation of Shampoo Composition (With Chamomile Extract and Urea)

The following components were combined to form an aqueous shampoo composition at an acidic pH.

|  | Parts (%) |
|---|---|
| Amphoteric Detergent (1) | 50.0 |
| Nonionic Amine Oxide Detergent (2) | 4.0 |
| Chamomile Extract (3) | 3.0 |
| Urea | 2.0 |
| Nonionic Emulsifier (4) | 1.5 |
| Perfume | 0.3 |
| Water to make | 100 parts total |

(1) Tegobetaine, an Amphoteric Detergent
(2) Aromox C/12W bis(2-hydroxyethyl)cocoamine oxide
(3) Chamomile Extract, German 25%
(4) Tween 20, Emulsifier, polyoxyethylene sorbitan monolaurate.

This resulted in a shampoo composition with a pH of about 5.75.

In this type formulation, pH adjustments may be made by the addition of varying small amounts of an organic acid such as citric acid.

EXAMPLE 3

Curl Retention Testing Method

For evaluation of the curl retention properties of the shampoo compositions, the method may be described as follows:

1. Swatches of hair about 7 inches long each weighing 1 gram are used.
2. The swatch is washed in water, excess water removed, and then soaked and agitated in the shampoo for 3 minutes.
3. It is then again washed with water and the excess water is removed.
4. The moist swatches are then rolled on identical curlers in the same pattern.
5. The hair is then dried in the hair drier for 90 minutes at about 50°C.
6. The swatches are then removed from the curlers and hung on graduated panels which are adapted to be able to measure and read the height of the curl in inches. Readings in inches are taken of the height of the curl initially and every 30 minutes for two hours.
7. After two hours the swatch is combed 5 times and is then measured again.

The percent curl retention is then calculated using the following formula:

$$\text{Percent Curl Retention} = \frac{L - L_t}{L - L_o} \times 100$$

$L$ = length of hair fully extended
$L_o$ = length of hair before exposure (or initial height of curl).
$L_t$ = length of hair after exposure for time "t" expressed in minutes and after five combings.

These tests are carried out at room temperature and relative humidity at a temperature of about 97° to 103°F.

Results are shown in the table which follows:

Table

| Formula | No. of Swatches | Curl Retention Results Height of Curl in Inches - After Time Shown ||||||  % Curl Retention | Condition Temp. & Relative Humidity | Type of Hair | Weight & Length of Swatch |
|---|---|---|---|---|---|---|---|---|---|---|---|
| | | Initial | 30 Min. | 60 Min. | 90 Min. | 120 Min. | After 5 Combings | | | | |
| Control Water | 30 | 0.62 | 3.19 | 3.45 | 3.62 | 3.80 | 4.12 | 45.1 | 97°F 48% | Natural Brown | 0.9 g 7" |
| Comp. of Ex. 1 | 30 | 0.70 | 2.82 | 3.05 | 3.09 | 3.13 | 3.56 | 54.6 | 98°F 51% | Natural Brown | 0.9 g 7" |
| Control Water | 40 | 0.62 | 0.71 | 0.84 | — | 0.91 | 1.64 | 84.0 | Ambient 73–76°F 22–33% | Ditto | Ditto |
| Comparison Shampoo | 25 | 0.70 | 0.80 | 0.86 | 0.94 | — | 1.40 | 88.8 | Ditto | Ditto | Ditto |
| Comp. of of Ex. 1 | 30 | 0.54 | 0.61 | 0.65 | 0.66 | 0.69 | 1.11 | 91.1 | Ditto | Ditto | Ditto |
| Comparison Urea Only | 15 | 0.98 | 1.05 | 1.18 | 1.2 | 1.26 | 1.8 | 83.6 | Ditto | Ditto | Ditto |
| Comparison Chamomile Only | 10 | 0.62 | 0.67 | 0.72 | 0.72 | 0.72 | 1.35 | 88.5 | Ditto | Ditto | Ditto |

What is claimed is:

1. An aqueous shampoo composition with curl retention properties which comprises as the major cleansing agent component an amphoteric detergent and minor amounts of a nonionic detergent and a combination of chamomile extract with urea or thiourea, said urea or thiourea being in the range of about 1 percent to 3 percent and said chamomile as a 25 percent extract being in a ratio in the range of 3 to 2 to said urea or thiourea.

2. The shampoo composition as in claim 1 where the pH of the composition is from about 4.5 to 6.5.

3. The shampoo composition as in claim 1 where the pH of the composition is from about 7.0 to 8.5.

4. The aqueous shampoo composition as in claim 1 containing from about 15 percent to 25 percent of an amphoteric detergent as the primary cleansing agent and 1 percent to 5 percent of chamomile extract with 2 percent of urea or thiourea, the pH of the composition being between about 4.5 and 8.5.

5. The shampoo composition as in claim 4 where the amphoteric detergent is a betaine.

* * * * *